United States Patent
Garde et al.

(10) Patent No.: US 10,252,012 B2
(45) Date of Patent: Apr. 9, 2019

(54) SYSTEM AND METHOD FOR CONTROLLING AIRWAY GAS PARAMETERS DURING HIGH FREQUENCY POSITIVE PRESSURE VENTILATION

(71) Applicant: KONINKLIJKE PHILIPS N.V., Eindhoven (NL)

(72) Inventors: Smita Garde, Irvine, CA (US); Samir Ahmad, San Diego, CA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 825 days.

(21) Appl. No.: 14/655,767

(22) PCT Filed: Jan. 9, 2014

(86) PCT No.: PCT/IB2014/058141
§ 371 (c)(1),
(2) Date: Jun. 26, 2015

(87) PCT Pub. No.: WO2014/111832
PCT Pub. Date: Jul. 24, 2014

(65) Prior Publication Data
US 2015/0335840 A1 Nov. 26, 2015

Related U.S. Application Data

(60) Provisional application No. 61/753,554, filed on Jan. 17, 2013.

(51) Int. Cl.
*A61M 16/00* (2006.01)
*A61M 16/20* (2006.01)

(52) U.S. Cl.
CPC .... *A61M 16/0009* (2014.02); *A61M 16/0003* (2014.02); *A61M 16/0069* (2014.02);
(Continued)

(58) Field of Classification Search
CPC ............ A61M 16/0009; A61M 16/024; A61M 16/208; A61M 16/0003; A61M 16/0069;
(Continued)

(56) References Cited

U.S. PATENT DOCUMENTS

| 5,165,398 A | 11/1992 | Bird |
| 6,390,092 B1 | 5/2002 | Leenhoven |

(Continued)

FOREIGN PATENT DOCUMENTS

| JP | 2001190671 A | 7/2001 |
| WO | 2007142642 A1 | 12/2007 |

(Continued)

*Primary Examiner* — Gregory Anderson
*Assistant Examiner* — Margaret Luarca

(57) ABSTRACT

The present disclosure pertains to a high frequency positive pressure ventilation system. The system may be configured to maintain a time-averaged airway pressure level at a target time-averaged airway pressure level and/or a peak-to-peak pressure difference at a target peak-to-peak pressure difference. In some embodiments, the system is configured to control the inspiratory subsystem, the expiratory flow generator and exhalation valve in accordance with a high frequency positive pressure ventilation therapy regime.

15 Claims, 3 Drawing Sheets

(52) U.S. Cl.
    CPC ...... *A61M 16/0096* (2013.01); *A61M 16/024* (2017.08); *A61M 16/208* (2013.01); *A61M 16/0057* (2013.01); *A61M 16/20* (2013.01); *A61M 2016/003* (2013.01); *A61M 2016/0027* (2013.01); *A61M 2205/3334* (2013.01); *A61M 2205/50* (2013.01)

(58) Field of Classification Search
    CPC .......... A61M 16/0096; A61M 2005/50; A61M 2205/3334
    See application file for complete search history.

(56) References Cited

U.S. PATENT DOCUMENTS

| | | | |
|---|---|---|---|
| 6,581,597 B2 | 6/2003 | Sugiura | |
| 2013/0220324 A1* | 8/2013 | Jafari | A61M 16/00 128/204.23 |
| 2013/0276789 A1* | 10/2013 | Garde | A61M 16/0051 128/204.23 |

FOREIGN PATENT DOCUMENTS

| | | | |
|---|---|---|---|
| WO | 2011073839 A2 | 6/2011 | |
| WO | 2012085792 A2 | 6/2012 | |

\* cited by examiner

SYSTEM AND METHOD FOR CONTROLLING AIRWAY GAS PARAMETERS DURING HIGH FREQUENCY POSITIVE PRESSURE VENTILATION

CROSS-REFERENCE TO PRIOR APPLICATIONS

This application is the U.S National Phase application under 35 U.S.C § 371 of International Application No. PCT/IB2014/05814,filed on Jan. 9, 2014, which claims the benefit of U.S. Provisional Patent Application No. 61/753,554, filed on Jan. 17,2013. These applications are hereby incorporated by reference herein.

BACKGROUND

1. Field

The present disclosure pertains to a high frequency positive pressure ventilation system. The system may be configured to maintain a time averaged airway pressure level at a target time averaged airway pressure level and/or a peak-to-peak pressure difference at a target peak-to-peak pressure difference.

2. Description of the Related Art

High frequency ventilators are known. High frequency ventilators are used for delivery of low tidal volumes of breathable gas. High frequency oscillatory ventilation (HFOV) is a widely used type high frequency ventilation that uses a piston based system for generating positive and negative pressure oscillations. In addition to manually selecting the frequency of the high frequency ventilation, a user typically manually selects a peak-to-peak pressure and a mean airway pressure. The peak-to-peak pressure and the mean airway pressure determine a delivered tidal volume and an oxygenation of a patient's lungs. In high frequency oscillatory ventilation, peak-to-peak pressure is controlled by piston settings and the mean airway pressure is controlled by a balloon valve in the expiratory limb. The user manually adjusts the settings of this valve as the conditions in the patient's lungs change.

SUMMARY

Accordingly, one or more aspects of the present disclosure relate to a high frequency positive pressure ventilation system. The system comprises an inspiratory subsystem, an expiratory flow generator, one or more sensors, an exhalation valve, and one or more processors. The inspiratory subsystem is configured to provide a pressurized flow of gas for delivery to the airway of the subject. The expiratory flow generator is configured to draw gas from the airway of a subject to a system outlet. The one or more sensors are configured to generate output signals conveying information related to one or more gas parameters at or near the airway of the subject. The exhalation valve is configured to selectively control flow from the airway of the subject though the expiratory flow generator. The one or more processors are configured to execute computer program modules. The computer program modules include a parameter module, a target module, and a control module. The parameter module is configured to determine the one or more gas parameters at or near the airway of the subject based on the output signals, the parameter module configured to determine a time averaged airway pressure level. The target module is configured to obtain target values for the one or more gas parameters, the target module being configured to obtain a target time averaged airway pressure level. The control module is configured to control the expiratory flow generator and the exhalation valve to maintain the time averaged airway pressure level at the target time averaged airway pressure level over a series of high frequency pressure cycles.

Yet another aspect of the present disclosure relates to a method for delivering high frequency positive pressure ventilation to a subject with a high frequency positive pressure ventilation system, the system comprising an inspiratorysubsystem, an expiratory flow generator, one or more sensors, an exhalation valve, and one or more processors, the one or more processors configured to execute computer program modules, the computer program modules comprising a parameter module, a target module, and a control module. The method comprises drawing gas from the airway of the subject to a system outlet with the expiratory flow generator; generating output signals conveying information related to one or more gas parameters at or near the airway of the subject with the one or more sensors; selectively controlling, with the exhalation valve, the flow of gas drawn from the airway of the subject by the expiratory flow generator; determining the one or more gas parameters at or near the airway of the subject based on the output signals with the parameter module, the one or more gas parameters including a time averaged airway pressure level; obtaining target values for the one or more gas parameters with the target module, the target values including a target time averaged airway pressure level; controlling the inspiratory subsystem, the expiratory flow generator and the exhalation valve with the control module to deliver a series of pressure cycles in accordance with a high frequency positive pressure ventilation therapy regime; and selectively controlling the exhalation valve and the expiratory flow generator with the control module to maintain the time averaged airway pressure level at the target time averaged airway pressure level over the series of pressure cycles.

Still another aspect of present disclosure relates to a high frequency positive pressure ventilation system. The system comprises means for generating a pressurized flow of breathable gas for delivery to the airway of the a subject; means for drawing gas out of the airway of the subject; means for generating output signals conveying information related to one or more gas parameters at or near the airway of the subject; means for regulating a rate at which gas is drawn out of the airway of the subject; means for determining the one or more gas parameters at or near the airway of the subject, the means for determining the one or more gas parameters configured to determine a time averaged airway pressure level; means for obtaining target values for the one or more gas parameters, the means for obtaining target values configured to obtain a target time averaged airway pressure level; and means for controlling the means for drawing and the means for regulating to deliver a series of pressure cycles in accordance with a high frequency positive pressure ventilation therapy regime such that the time averaged airway pressure level is maintained at the time averaged airway pressure level at the target time averaged airway pressure level over the series of pressure cycles.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
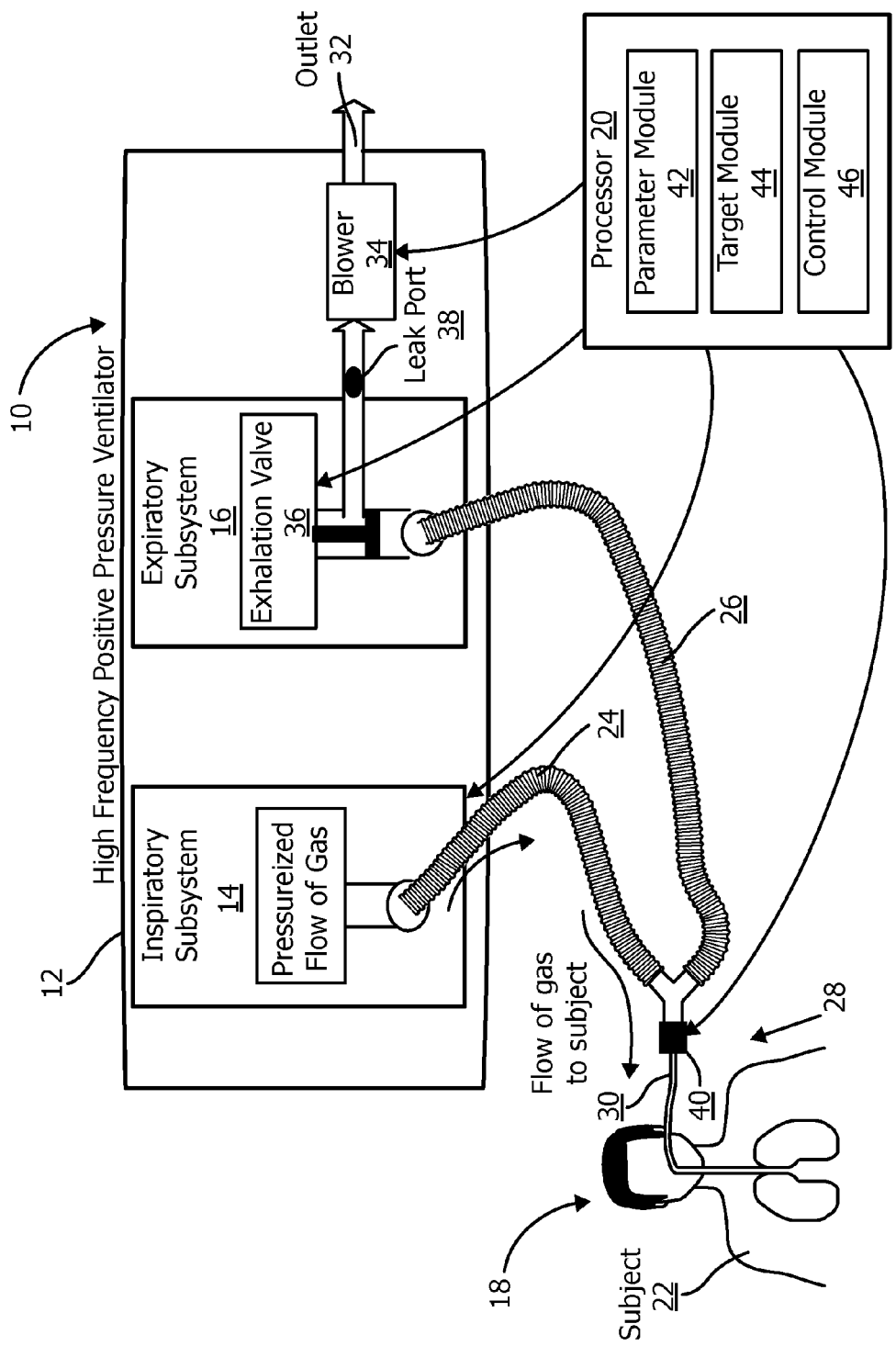
FIG. 1 is a schematic illustration of a high frequency positive pressure ventilation system.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 schematically illustrates a high frequency positive pressure ventilation system 10. In some embodiments, system 10 comprises one or more of a ventilator 12 that includes an inspiratory subsystem 14, an expiratory subsystem 16, a respiratory circuit 18, a processor 20, electronic storage (not shown), and/or other components. In some embodiments, system 10 is configured to provide a subject 22 with ventilation in accordance with a high frequency positive pressure ventilation therapy regime. System 10 is configured to maintain a time averaged airway pressure level (e.g., mean airway pressure) and/or a peak-to-peak pressure level at target levels over a series of inhalations and/or exhalations. System 10 is configured to automatically maintain the time averaged airway pressure level and/or the peak-to-peak pressure level, reducing and/or eliminating the need for manual adjustments during high frequency positive pressure ventilation. Automatic control provides timely parameter adjustments as lung and respiratory conditions change during treatment.

Respiratory circuit 18 is configured to deliver a pressurized flow of breathable gas to the airway of the subject in order to ventilate subject 22. Respiratory circuit 18 includes one or more of an inspiratory conduit 24, an expiratory circuit 26, a subject interface 28, and/or other components.

Inspiratory conduit 24 is configured to deliver gas for inspiration from inspiratory subsystem 14 to subject interface 28. Expiratory conduit is configured to communicate expired gas to expiratory subsystem 16 from subject interface 28. Conduits 24 and/or 26 may be flexible, and/or may be selectively removable from subject interface 28, inspiratory subsystem 14, and/or expiratory subsystem 16. Subject interface 28 includes a subject interface appliance 30 that communicates with the airway of subject 22. Subject interface appliance 30 may include an invasive appliance, such as an endotracheal tube or other invasive appliance, or a non-invasive appliance, such as a mask or other non-invasive appliance.

Inspiratory subsystem 14 is configured to provide a pressurized flow of breathable gas for delivery to the airway of subject 22 during inspiration. Inspiratory subsystem 14 is configured such that one or more gas parameters of the pressurized flow of breathable gas are controlled in accordance with a therapy regime. The one or more gas parameters may include, for example, one or more of flow, pressure, humidity, velocity, acceleration, and/or other parameters. In some embodiments, system 10 is a device dedicated to high frequency positive pressure ventilation. In some embodiments, Inspiratory subsystem 14 is a ventilator and/or positive airway pressure device configured to provide therapy other than and/or in addition to high frequency positive pressure ventilation. Inspiratory subsystem 14 may include any device, such as, for example, a pump, compressed gas source, blower, piston, or bellows, that is capable of providing a flow of gas at an elevated pressure. The present disclosure also contemplates that gas other than ambient atmospheric air (e.g., oxygen enriched gas, medicament, and/or other gases) may be introduced into system 10 for delivery to subject 22.

Expiratory subsystem 16 is configured to exhaust gas from the airway of subject 22 and/or respiratory circuit 18 to effect expiration of gas. Expiratory subsystem 16 may include one or more of an outlet 32, an expiratory flow generator 34, an exhalation valve 36, and/or other components. Outlet 32 is configured to release expired gas from system 10. This may include releasing gas directly into ambient atmosphere, or releasing gas into a filter or other treatment component to treat the gas prior to release. The expiratory flow generator 34 is configured to draw gas through expiration conduit 26 and out outlet 32. The expiratory flow generator 34 may include, for example, a blower, a bellows, and/or other devices or mechanisms suitable for generating a flow of gas from expiration conduit 26 out through outlet 32. The rate at which expiratory flow generator 34 creates the flow may be adjustable by adjusting the operation of expiratory flow generator 34. For example, a rotary speed of a blower may be adjusted to draw more or less gas out through outlet 32.

Figure 2:
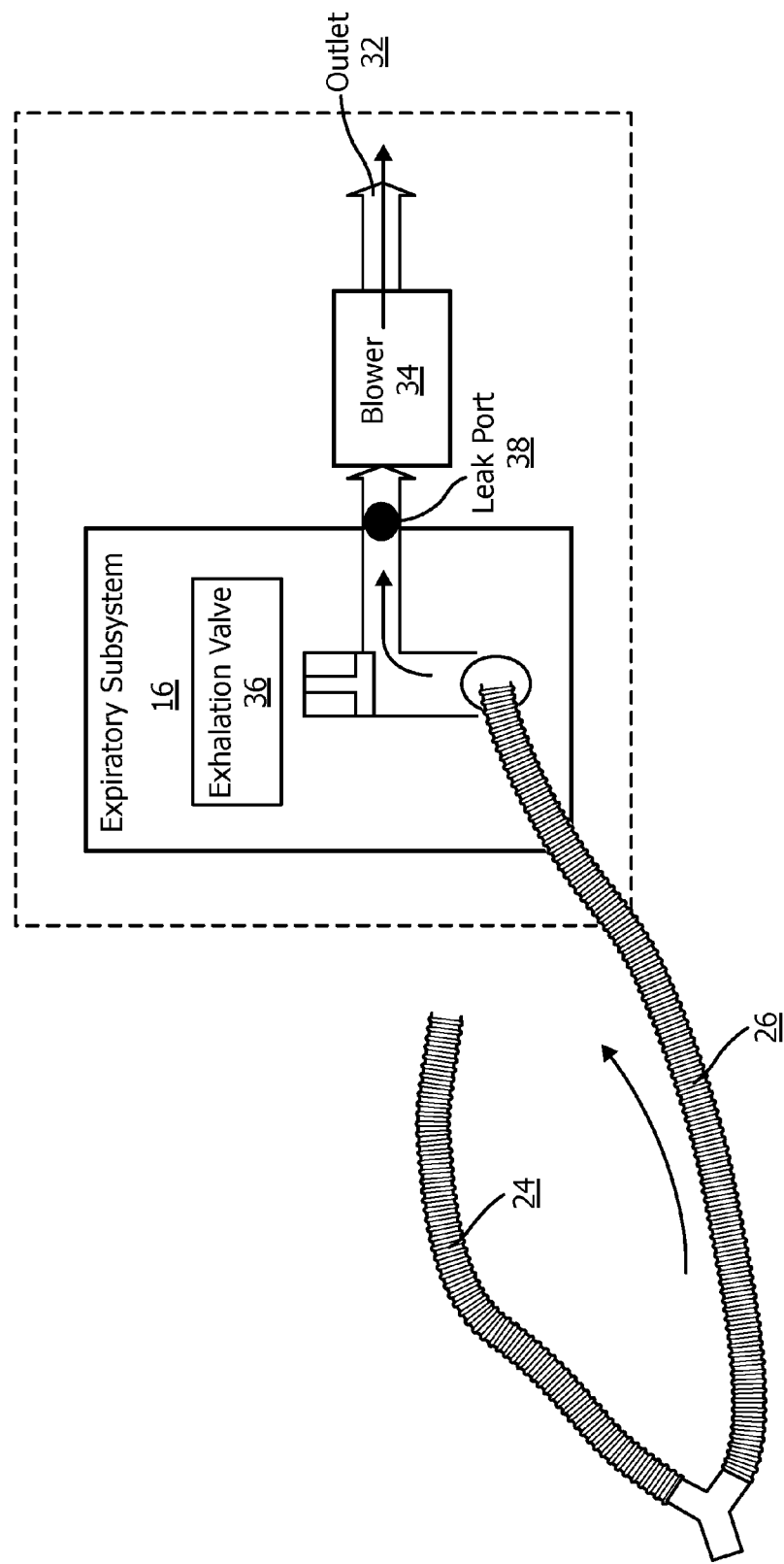
FIG. 2 is a schematic illustration of a portion of a high frequency positive pressure ventilation system.

Exhalation valve 36 is configured to selectively place expiratory conduit 26 in communication with expiratory flow generator 34. In a first position (shown in FIG. 1), exhalation valve 36 may inhibit or completely shut off communication between expiratory conduit 26 and expiratory flow generator 34. At the first position, pressure in the airway of subject 22 will tend to rise as gas from inspiratory subsystem 14 is delivered to subject 22 while little or no gas is permitted to be exhausted through expiratory subsystem 14. FIG. 2 illustrates exhalation valve 36 in a second position in which expiratory conduit 26 communicates with expiratory flow generator 34 through exhalation valve 36. This may cause pressure in the airway of subject 22 to fall, as gas from the airway of subject 22 is drawn out through expiratory conduit 26 and outlet 32.

Returning to FIG. 1, when exhalation valve 36 is in the first position shown in FIG. 1, and expiratory flow generator 34 is running to push a flow out through outlet 32, a leak port 38 may act as an inlet through which gas is drawn into expiratory flow generator 34. Leak port 38 may simply be a passive port (e.g., an opening, a flapper valve, and/or other passive ports), or may be actively opened as exhalation valve 36 is closed, and vice versa. In some embodiments, exhalation valve 36 is not merely opened and closed, but may be opened and closed incrementally to allow relatively more or less gas to flow from expiratory conduit 26 to outlet 32.

It will be appreciated from the foregoing, that by controlling exhalation valve 36 and/or expiratory flow generator 34, pressure at the airway of subject 22 can be controlled while gas is delivered to the airway of subject 22 from inspiratory subsystem 14. The parameters (e.g., pressure, flow, etc.) of the gas delivered from inspiratory subsystem 14 may be controlled dynamically in coordination with exhalation valve 36 and/or expiratory flow generator 34 to control airway pressure, or the inspiratory gas may be delivered substantially continuously and airway pressure controlled entirely or substantially entirely by adjusting operation of exhalation valve 36 and/or expiratory flow generator 34.

By way of a non-limiting example, expiratory flow generator 34 and/or exhalation valve 36 may be configured to adjust the airway pressure in accordance with a high frequency ventilation regime. In some embodiments, the therapy regime may dictate that the airway pressure fluctuates over a series of pressure cycles in which a mean airway pressure is maintained. During these pressure cycles, the parameters such as frequency, pressure or flow amplitude, mean pressure, tidal volume, peak flow, and/or other parameters can be controlled through operation of expiratory flow generator 34 and/or exhalation valve 36.

System 10 may include one or more sensors 40 configured to generate output signals conveying information related to one or more gas parameters of the gas within system 10. The one or more gas parameters may comprise flow, volume, pressure, a composition (e.g., concentration(s) of one or more constituents), temperature, humidity, acceleration, velocity, acoustics, changes in a parameter indicative of respiration, and/or other gas parameters. Sensors 40 may comprise one or more sensors that measure such parameters directly. Sensors 40 may comprise one or more sensors that generate output signals related to one or more parameters of the flow of gas indirectly. For example, one or more of sensors 40 may generate an output based on an operating parameter of expiratory flow generator 34 (e.g., motor current, voltage, rotational velocity, and/or other operating parameters), and/or other parameters. Although sensors 40 are illustrated at a single location within respiratory circuit 18, this is not intended to be limiting. Sensors 40 may include sensors disposed in a plurality of locations, such as for example, within expiratory flow generator 34, within (or in communication with) inspiratory subsystem 14, and/or other locations.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some implementations, processor 20 may comprise a plurality of processing units. These processing units may be physically located within the same device, or processor 20 may represent processing functionality of a plurality of devices operating in coordination.

As shown in FIG. 1, processor 20 is configured to execute one or more computer program modules. The one or more computer program modules may comprise one or more of a parameter module 42, a target module 44, a control module 46, and/or other modules. Processor 20 may be configured to execute modules 42, 44, and/or 46 by software; hardware; firmware; some combination of software, hardware, and/or firmware; and/or other mechanisms for configuring processing capabilities on processor 24.

It should be appreciated that although modules 42, 44, and/or 46 are illustrated in FIG. 1 as being co-located within a single processing unit, in implementations in which processor 20 comprises multiple processing units, one or more of modules 42, 44, and/or 46 may be located remotely from the other modules. The description of the functionality provided by the different modules 42, 44, and/or 46 described below is for illustrative purposes, and is not intended to be limiting, as any of modules 42, 44, and/or 46 may provide more or less functionality than is described. For example, one or more of modules 42, 44, and/or 46 may be eliminated, and some or all of its functionality may be provided by other modules 42, 44, and/or 46. As another example, processor 20 may be configured to execute one or more additional modules that may perform some or all of the functionality attributed below to one of modules 42, 44, and/or 46.

Parameter module 42 is configured to determine one or more parameters within system 10. The one or more parameters within system 10 may comprise gas parameters related to the flow of breathable gas at or near the airway of subject 22, and/or other parameters. Parameter module 42 is configured to determine the one or more parameters based on the output signals of sensors 40, and/or other information. The information determined by parameter module 42 may be used for controlling expiratory flow generator 34, controlling exhalation valve 36, stored in electronic storage, and/or used for other uses. The one or more gas parameters of the pressurized flow of breathable gas may comprise, for example, one or more of a flow rate, a volume, a pressure, humidity, temperature, acceleration, velocity, and/or other gas parameters.

In some embodiments, parameter module 42 may be configured to determine the respiratory phase (e.g., inhalation, exhalation) and/or or high frequency pressure cycles during ventilation of subject 12. The respiratory phase may include the phase of the determinations made by parameter module 25 are based on the output signals from pressure cycles generated through control of inspriatory subsystem 14, expiratory flow generator 34 and/or exhalation valve 36. Parameter module 42 may be configured to determine additional respiratory parameters related to the respiration of subject 22. Additional respiratory parameters related to the respiration of subject 22 may comprise a tidal volume, a timing (e.g., beginning and/or end of inhalation, beginning and/or end of exhalation, etc.), a respiration rate, a duration (e.g., of inhalation, of exhalation, of a single breathing cycle, etc.), respiration frequency, the frequency of high frequency pressure cycles, mean airway pressure and/or other respiratory parameters. The respiratory phase determinations may be used by control module 46 to control expiratory flow generator 34 and/or exhalation valve 36 to control the airway pressure of subject 22, may be stored in electronic storage, and/or used for other uses. In some embodiments, parameter module 42 is configured to determine the respiratory phase (e.g., inhalation, exhalation) based on changes in pressure, flow rate, and/or other parameters determined by parameter module 42.

Parameter module 42 may be configured to determine a time averaged airway pressure level. The time averaged airway pressure level may be the mean airway pressure, for example. In some embodiments, the time averaged airway pressure level may be averaged continuously during a therapy session. A current time averaged airway pressure level may be determined based on a previously determined time averaged airway pressure level and the current output signals from sensors 40. In some embodiments, the time averaged airway pressure level may be determined during a therapy window. For example, the time averaged airway pressure level may be averaged over a therapy window of the two (or more) most recent high frequency ventilation cycles. In some embodiments the averaged may be over a predetermined amount of time just prior to the current high frequency ventilation cycle.

Parameter module 42 may be configured to determine a peak-to-peak pressure difference based on the output signals. In some embodiments, the peak-to-peak pressure difference may be related to differences between two or more consecutive maximum pressures in a cyclic pressure wave generated by the operation of inspiratory subsystem 14, expiratory flow generator 34 and/or exhalation valve 36 according to the high frequency positive pressure ventilation therapy regime. In some embodiments, the peak-to-peak pressure difference may be determined continuously during a therapy session. A current peak-to-peak pressure difference may be determined based on a previously determined peak pressure level and a current peak pressure level indicated by the output signals from sensors 40.

In some embodiments, a frequency of the determinations, algorithms used to determine the parameters, and/or other factors related to determination of the gas parameters by parameter module 25 may be determined at manufacture, determined based on user input via a user interface, determined based on previous and/or current respiration by the subject, determined based on the therapy regime, and/or determined in other ways.

Target module 44 is configured to obtain target values for the one or more gas parameters. Target module 44 is configured to obtain a target time averaged airway pressure level. In some embodiments, the target time averaged airway pressure level may be a mean airway pressure level. Target module 44 is configured to obtain a target peak-to-peak pressure difference. In some embodiments, target module 44 is configured to determine the target values for the gas parameters based on previous respiration of the subject. In some embodiments, the target values for the gas parameters may be determined at manufacture. In some embodiments, target module 44 may obtain the target values for the gas parameters based on information entered by the subject and/or other users (e.g., a caregiver, a doctor) via a user interface. In some embodiments, target module 27 may obtain the target values via other methods.

Control module 46 is configured to control inspiratory subsystem 14, expiratory flow generator 34 and/or exhalation valve 36 to provide an airway pressure in accordance with a high frequency positive pressure ventilation therapy regime. Control module 46 is configured to control the inspiratory subsystem 14, the expiratory flow generator 34 and/or exhalation valve 36 in accordance with the high frequency positive pressure ventilation therapy regime based on the output signals from sensors 40. Control module 46 is configured to control inspiratory subsystem 14, expiratory flow generator 34 and/or exhalation valve to cause airway pressure cycles at a frequency between about 3 Hz and about 25 Hz. Control module 46 is configured to control inspiratory subsystem 14, expiratory flow generator 34 and/or exhalation valve 36 such that a tidal volume of the pressurized flow of breathable gas is about 6 ml/kg for a patient.

In some embodiments, control module 46 is configured to selectively control inspiratory subsystem 14, expiratory flow generator 34 and/or exhalation valve 36 to maintain the time averaged airway pressure level at the target time averaged airway pressure level over a number of pressure cycles. The individual cycles may correspond to an inhalation and exhalation by the subject. In some embodiments, the time averaged airway pressure level may be the mean airway pressure. Control module 46 is configured to selectively inspiratory subsystem 14, expiratory flow generator 34 and/or exhalation valve 36 to maintain the time averaged airway pressure level at the target time averaged airway pressure level based on the output signals, the information determined by parameter module 42, the information obtained by target module 44, and/or other information.

By way of a non-limiting example, an airway pressure may be determined and averaged over few high frequency positive pressure cycles by parameter module 42. The number of pressure cycles for which the pressure is averaged may depend on the frequency of the high frequency ventilation. The difference (or error for example) between a target mean airway pressure (obtained by target module 44) and a current mean airway pressure may be determined by control module 46. Based on the determined difference, control module 46 may simultaneously 1) control an extent to which exhalation valve 36 is opened and/or closed, increase and/or decrease the current/speed of a blower of expiratory flow generator 34, and/or control other aspects of the operation of system 10 to impact airway pressure. If, for example, the current mean airway pressure is higher than the target mean airway pressure, control module 46 may control the blower speed to increase such that negative pressure is increased during expiration. In addition, control module 46 may control exhalation valve 36 to open partially to facilitate faster changes to the negative pressure during exhalation.

In some embodiments, control module 46 is configured to selectively control expiratory flow generator 34 and/or exhalation valve 36 to maintain the peak-to-peak pressure difference at the target peak-to-peak pressure difference over the pressure cycles. Control module 46 is configured to selectively control expiratory flow generator 34 and/or exhalation valve 36 to maintain the peak-to-peak pressure difference at the target peak-to-peak pressure difference based on the output signals, the information determined by parameter module 42, the information obtained by target module 44, and/or other information. In some embodiments, control module 46 may be configured to compare a current peak-to-peak pressure difference to the target peak-to-peak pressure difference expiratory flow generator 34, the exhalation valve 36, and/or other components of system 10 based on the comparison. Control module 29 may be configured to control valve 18, valve 20, and/or inspiratory flow generator 14 substantially simultaneously to maintain the peak-to-peak pressure at the target peak-to-peak pressure.

In some embodiments, control module 46 is configured to maintain the time averaged airway pressure level at the target time averaged airway pressure level, and the peak-topeak pressure difference at the target peak-to-peak pressure difference, during the same series of pressures cycles.

In some embodiments, control module 46 is configured to control inspiratory subsystem 14, expiratory flow generator 34, exhalation valve 36, and/or other devices to generate the flow of gas in accordance with a ventilator regime, a positive airway pressure therapy regime, and/or other therapy regimes in addition to and/or instead of the high frequency positive pressure support therapy regime.

Figure 3:
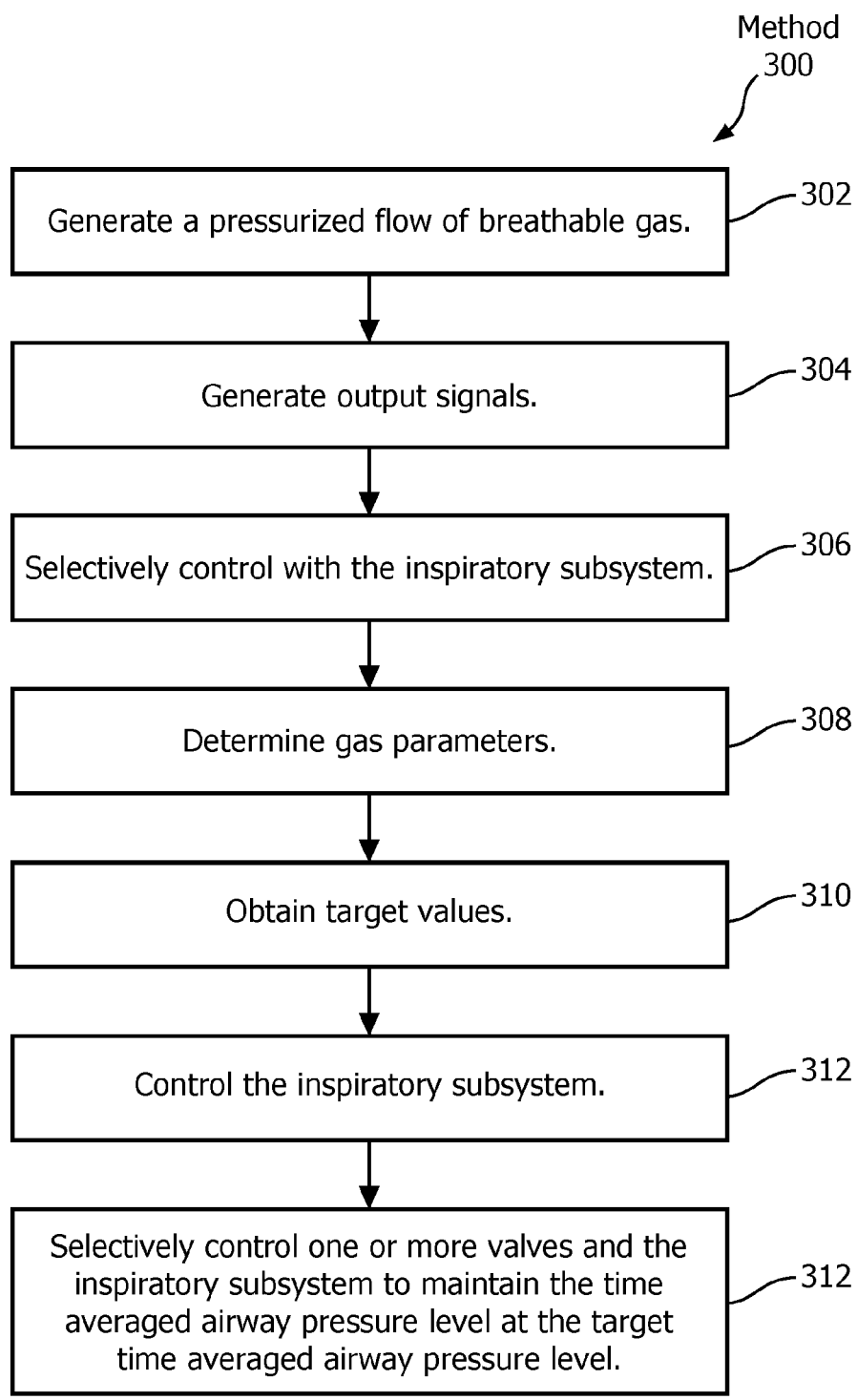
FIG. 3 is a method for delivering high frequency positive pressure ventilation to a subject with a high frequency positive pressure ventilation system.

FIG. 3 illustrates a method 300 for delivering high frequency positive pressure ventilation to a subject with a high frequency positive pressure ventilation system. The system comprises an inspiratory subsystem, an expiratory flow generator, one or more sensors, an exhalation valve, and one or more processors, and/or other components. The one or more processors are configured to execute computer program modules. The computer program modules comprise a parameter module, a target module, and a control module. The operations of method 300 presented below are intended to be illustrative. In some embodiments, method 300 may be accomplished with one or more additional operations not described, and/or without one or more of the operations discussed. Additionally, the order in which the operations of method 300 are illustrated in FIG. 3 and described below is not intended to be limiting.

In some embodiments, method 300 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 300 in response to instructions stored electronically on an electronic storage medium. The one or more processing devices may include one or more devices configured through hardware, firmware, and/or software to be specifically designed for execution of one or more of the operations of method 300.

At an operation 302, a pressurized flow of breathable gas for delivery to the airway of the subject is generated with the inspiratory subsystem similar to inspiratory subsystem 14 (shown in FIG. 1 and described herein). In some embodiments, operation 302 is performed at least in part by a expiratory flow generator and/or an exhalation valve the same as or similar to expiratory flow generator 34 and/or exhalation valve 36, respectively (shown in FIG. 1 and described herein).

At an operation 304, output signals conveying information related to one or more gas parameters of the pressurized flow of breathable gas are generated with the one or more sensors. In some embodiments, operation 304 is performed by one or more sensors the same as or similar to sensors 40 (shown in FIG. 1 and described herein).

At an operation 306, the airway pressure of the subject is selectively controlled with the inspiratory subsystem, the expiratory flow generator and/or the one or more valves. In some embodiments, operation 306 is performed at least in part by a inspiratory subsystem, an expiratory flow generator and/or an exhalation valve the same as or similar to inspiratory subsystem 14, expiratory flow generator 34 and/or exhalation valve 36, respectively (shown in FIG. 1 and described herein).

At an operation 308, the one or more gas parameters of the pressurized flow of breathable gas at or near the airway of the subject are determined based on the output signals with the parameter module. In some embodiments, the one or more gas parameters include a time averaged airway pressure level. In some embodiments, the one or more gas parameters may include a peak-to-peak pressure difference. In some embodiments, operation 308 is performed by a processor module the same as or similar to parameter module 42 (shown in FIG. 1 and described herein).

At an operation 310, target values for the one or more gas parameters are obtained with the target module. In some embodiments, the target values include a target time averaged airway pressure level. In some embodiments, the one or more gas parameters may include a target peak-to-peak pressure difference. In some embodiments, operation 310 is performed by a processor module the same as or similar to target module 44 (shown in FIG. 1 and described herein).

At an operation 312, the inspiratory subsystem, the expiratory flow generator and/or the exhalation valve may be controlled with the control module to generate the pressurized flow of breathable gas in accordance with a high frequency positive pressure ventilation therapy regime. In some embodiments, operation 312 is performed by a processor module the same as or similar to control module 46 (shown in FIG. 1 and described herein).

At an operation 314, the inspiratory subsystem, the expiratory flow generator and/or the exhalation valve may be selectively controlled with the control module to maintain the time averaged airway pressure level at the target time averaged airway pressure level over a series of positive and negative pressures. In some embodiments, the inspiratory subsystem, the expiratory flow generator and/or the exhalation valve may be selectively controlled with the control module to maintain the peak-to-peak pressure difference at the target peak-to-peak pressure difference over a series of pressure cycles. In some embodiments, the time averaged airway pressure level and the peak-to-peak pressure difference may be maintained at their respective target levels at the same phases of the pressure cycles. In some embodiments, operation 314 is performed by a processor module the same as or similar to control module 46 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A high frequency positive pressure ventilation system, the system comprising:

an inspiratory subsystem to generate a pressurized flow of breathable gas for delivery to the airway of the subject;
an expiratory flow generator configured to draw gas from the airway of a subject to a system outlet during an exhalation;
one or more sensors configured to generate output signals conveying information related to one or more gas parameters at or near the airway of the subject;
an exhalation valve configured to selectively control flow from the airway of the subject though the expiratory flow generator;
one or more processors configured to execute computer program modules, the computer program modules comprising:
a parameter module configured to determine the one or more gas parameters at or near the airway of the subject based on the output signals, the parameter module configured to determine a time averaged airway pressure level;
a target module configured to obtain target values for the one or more gas parameters, the target module configured to obtain a target time averaged airway pressure level; and
a control module configured to control the inspiratory subsystem, the expiratory flow generator and the exhalation valve to maintain the time averaged airway pressure level at the target time averaged airway pressure level over a series of high frequency pressure cycles,
the control module further configured to control the time averaged airway pressure level during the exhalation with the expiratory flow generator and to facilitate a rate of change in the airway pressure during the exhalation with the exhalation valve, and further wherein the control module is configured to control the exhalation valve to open partially to facilitate faster changes in the airway pressure during the exhalation.

2. The system of claim 1, wherein the parameter module is further configured to determine a peak-to-peak pressure difference over the series of high frequency pressure cycles based on the output signals;
wherein the target module is further configured to obtain a target peak-to-peak pressure difference; and
wherein the control module is further configured to selectively control the inspiratory subsystem, the expiratory flow generator and the exhalation valve to maintain the peak-to-peak pressure difference at the target peak-to-peak pressure difference over the series of high frequency pressure cycles.

3. The system of claim 2, wherein the parameter module is configured such that the peak-to-peak pressure difference is related to a difference between two or more consecutive maximum pressures.

4. The system of claim 1, wherein the control module is configured to control the inspiratory subsystem, the expiratory flow generator and the exhalation valve to deliver the positive pressure ventilation at a frequency between about 3 Hz and about 25 Hz.

5. The system of claim 1, wherein the control module is configured to control the inspiratory subsystem, the expiratory flow generator and the exhalation valve such that a tidal volume of the pressurized flow of breathable gas is about 6 ml/kg.

6. A method of operating a high frequency positive pressure ventilation system for delivering high frequency positive pressure ventilation to a subject, the system comprising an inspiratory subsystem, an expiratory flow generator, one or more sensors, an exhalation valve, and one or more processors, the one or more processors configured to execute computer program modules, the computer program modules comprising a parameter module, a target module, and a control module, the method comprising:
generating a pressurized flow of breathable gas for delivery to the airway of the subject with the inspiratory subsystem;
drawing gas from the airway of the subject to a system outlet with the expiratory flow generator;
generating output signals conveying information related to one or more gas parameters at or near the airway of the subject with the one or more sensors;
selectively controlling, with the inspiratory subsystem, the exhalation valve, the flow of gas drawn from the airway of the subject by the expiratory flow generator;
determining the one or more gas parameters at or near the airway of the subject based on the output signals with the parameter module, the one or more gas parameters including a time averaged airway pressure level;
obtaining target values for the one or more gas parameters with the target module, the target values including a target time averaged airway pressure level;
controlling the inspiratory subsystem, the expiratory flow generator and the exhalation valve with the control module to deliver a series of pressure cycles in accordance with a high frequency positive pressure ventilation therapy regime; and
selectively controlling the inspiratory subsystem, the exhalation valve and the expiratory flow generator with the control module to maintain the time averaged airway pressure level at the target time averaged airway pressure level over the series of pressure cycles, wherein the selectively controlling step further comprises controlling the airway pressure during the drawing step with the expiratory flow generator, controlling a rate of change in the airway pressure during the drawing step with the exhalation valve, and controlling the exhalation valve to open partially to facilitate faster changes in the airway pressure during the exhalation.

7. The method of claim 6, further comprising:
determining a peak-to-peak pressure difference over the series of pressure cycles based on the output signals with the parameter module;
obtaining a target peak-to-peak pressure difference with the target module; and
selectively controlling the inspiratory subsystem, the exhalation valve and the expiratory flow generator with the control module to maintain the peak-to-peak pressure difference at the target peak-to-peak pressure difference over the series pressure cycles.

8. The method of claim 7, wherein the peak-to-peak pressure difference is related to a difference between two or more consecutive maximum pressures.

9. The method of claim 6, wherein the series of pressure cycles have a frequency between about 3Hz and about 25Hz.

10. The method of claim 6, further comprising controlling the inspiratory subsystem, the expiratory flow generator and the one or more valves such that a tidal volume of the pressurized flow of breathable gas is about 6 ml/kg.

11. A high frequency positive pressure ventilation system, the system comprising:
means for generating a pressurized flow of breathable gas for delivery to the airway of the a subject;
means for drawing gas out of the airway of the subject during an exhalation;

means for generating output signals conveying information related to one or more gas parameters at or near the airway of the subject;
means for regulating a rate at which gas is drawn out of the airway of the subject;
means for determining the one or more gas parameters at or near the airway of the subject, the means for determining the one or more gas parameters configured to determine a time averaged airway pressure level;
means for obtaining target values for the one or more gas parameters, the means for obtaining target values configured to obtain a target time averaged airway pressure level; and
means for controlling the means for generating, the means for drawing and the means for regulating to deliver a series of pressure cycles in accordance with a high frequency positive pressure ventilation therapy regime such that the time averaged airway pressure level is maintained at the time averaged airway pressure level at the target time averaged airway pressure level over the series of pressure cycles,
the means for controlling further configured to control the time averaged airway pressure level during the exhalation with the means for drawing gas out of the airway, to facilitate a rate of change in the time averaged pressure level during the exhalation with the means for regulating, the means for regulating further configured to control an exhalation valve to open partially to facilitate faster changes in an airway pressure during the exhalation.

12. The system of claim 11, wherein the means for determining the one or more gas parameters is further configured to determine a peak-to-peak pressure difference over the series of pressure cycles based on the output signals;
wherein the means for obtaining target values is further configured to obtain a target peak-to-peak pressure difference; and
wherein the means for selectively controlling are further configured to selectively control the means for generating, the means for drawing and the means for regulating to maintain the peak-to-peak pressure difference at the target peak-to-peak pressure difference over the series of pressure cycles.

13. The system of claim 12, wherein the means for determining the one or more gas parameters is configured such that the peak-to-peak pressure difference is related to a difference between two or more consecutive maximum pressures.

14. The system of claim 11, wherein the means for selectively controlling is configured such that a frequency of the series of pressure cycles is between about 3Hz and about 25Hz.

15. The system of claim 11, wherein the means for selectively controlling is configured such that a tidal volume of the individual pressure cycles is about 6 ml/kg.

* * * * *